(12) United States Patent
Tufts et al.

(10) Patent No.: US 9,205,109 B2
(45) Date of Patent: Dec. 8, 2015

(54) COPPER SALTS OF ION EXCHANGE MATERIALS FOR USE IN THE TREATMENT AND PREVENTION OF INFECTIONS

(71) Applicant: CAREFUSION 2200, INC., San Diego, CA (US)

(72) Inventors: Scott A. Tufts, El Paso, TX (US); James Bardwell, El Paso, TX (US); Michael J. Baltezor, Lee's Summit, MO (US)

(73) Assignee: CAREFUSION 2200, INC., San Diego, CA (US)

( * ) Notice: Subject to any disclaimer, the term of this patent is extended or adjusted under 35 U.S.C. 154(b) by 132 days.

(21) Appl. No.: 13/747,165

(22) Filed: Jan. 22, 2013

(65) Prior Publication Data

US 2013/0236564 A1 Sep. 12, 2013

Related U.S. Application Data

(63) Continuation of application No. 13/508,481, filed as application No. PCT/US2010/055599 on Nov. 5, 2010, now abandoned.

(60) Provisional application No. 61/258,789, filed on Nov. 6, 2009.

(51) Int. Cl.
| | |
|---|---|
| *A61K 33/34* | (2006.01) |
| *A61K 31/717* | (2006.01) |
| *A61L 15/18* | (2006.01) |
| *A61L 15/22* | (2006.01) |
| *C08L 1/08* | (2006.01) |
| *A61L 26/00* | (2006.01) |

(52) U.S. Cl.
CPC .............. *A61K 33/34* (2013.01); *A61K 31/717* (2013.01); *A61L 26/0004* (2013.01); *A61L 26/0023* (2013.01); *C08L 1/08* (2013.01)

(58) Field of Classification Search
CPC .. A61K 31/717; A61K 33/34; A61L 26/0004; A61L 26/0023; C08L 1/08
See application file for complete search history.

(56) References Cited

U.S. PATENT DOCUMENTS

| 5,098,417 | A | | 3/1992 | Yamazaki et al. |
|---|---|---|---|---|
| 5,888,526 | A | | 3/1999 | Tsubai et al. |
| 6,124,374 | A | * | 9/2000 | Kolias et al. ............... 523/120 |
| 2004/0241213 | A1 | | 12/2004 | Bray |
| 2006/0165745 | A1 | | 7/2006 | Chew et al. |
| 2007/0243263 | A1 | | 10/2007 | Trogolo |
| 2008/0057134 | A1 | | 3/2008 | Crudden |
| 2008/0305138 | A1 | | 12/2008 | Cullen et al. |
| 2008/0311165 | A1 | | 12/2008 | Gabbay |
| 2010/0266646 | A1 | | 10/2010 | Dvorak et al. |

FOREIGN PATENT DOCUMENTS

| GB | 1 333 906 A | 10/1973 |
|---|---|---|
| WO | WO 96/00321 A1 | 1/1996 |

OTHER PUBLICATIONS

Gabbay et al., "Novel Applications of Copper Oxide in Medicine: From Preventing Infection to Wound Healing", Metal Ions in Biology and Medicine, 2008, pp. 792-795, vol. 10.
Krahwinkel et al., "Topical and Systematic Medications for Wounds", Veterinary Clinics: Small Animal Practice, 2006, 739-757, vol. 36.
Sibikina et al., "Polysaccharide Complexes With Metal Cations: Structure and Application (A Review)", Pharmaceutical Chemistry Journal, 2009, pp. 341-345, vol. 43, No. 6.
Grissbach R., "Theory and Practice of Ion Exchange", -M.:1693, p. 171, 1 page.
Russian Office Action mailed Feb. 26, 2015 for corresponding Russian Patent Application No. 2012122578, 4 pages.

* cited by examiner

*Primary Examiner* — Abigail Fisher
(74) *Attorney, Agent, or Firm* — Arent Fox LLP

(57) ABSTRACT

Copper salts of ion exchange materials provide copper ions at levels suitable for use as an anti-infective agent. The copper salts of ion exchange materials may be formed using ether and ester derivatives of cellulose, such as carboxymethyl cellulose (CMC), ethylcellulose (EC), methylcellulose (MC), hydroxypropyl cellulose (HPC), hydroxypropyl methyl cellulose (HPMC), hydroxyethyl methyl cellulose (HEMC), cellulose acetate, and cellulose triacetate. Wound dressings having copper salts of ion exchange materials incorporated therein are also provided, and may be used to reduce the incidence of infection in wounds. The wound dressings may also be used to prevent infections in long-term wounds, such as those formed at wound drain, catheter, and ostomy entry sites. Copper salts of ion exchange materials may be used to kill microorganisms, and may optionally be used with additional anti-infective agents.

6 Claims, 3 Drawing Sheets

COPPER SALTS OF ION EXCHANGE MATERIALS FOR USE IN THE TREATMENT AND PREVENTION OF INFECTIONS

CROSS-REFERENCE TO RELATED APPLICATION

This application is a Continuation of U.S. application Ser. No. 13/508,481, filed May 7, 2012, which claims priority to International Application No. PCT/US2010/055599, filed Nov. 5, 2010, which claims priority to U.S. Provisional Patent Application No. 61/258,789, filed Nov. 6, 2009. The disclosures of the prior applications are hereby incorporated herein in their entirety by reference.

BACKGROUND OF THE INVENTION

1. Field of the Invention

The present invention relates generally to copper salts of ion exchange materials that provide copper ions at levels suitable for use as an anti-infective agent. In certain aspects of the invention, copper salts of cellulose derivatives are provided. The copper salts of ion exchange materials may be formed using ether and ester derivatives of cellulose, such as carboxymethyl cellulose (CMC), ethylcellulose (EC), methylcellulose (MC), hydroxypropyl cellulose (HPC), hydroxypropyl methyl cellulose (HPMC), hydroxyethyl methyl cellulose (HEMC), cellulose acetate, and cellulose triacetate. The present invention also relates to wound dressings having copper salts of ion exchange materials incorporated therein. The copper salts of ion exchange materials may produce an equilibrium of copper ions in a wound at a level that is therapeutically-effective for preventing infection. Wound dressings containing copper salts of ion exchange materials may be used in accordance with methods of reducing the incidence of infection in wounds such as lacerations, abrasions, and burns. The wound dressings may also be used in accordance with methods for preventing infections in long-term wounds, such as those formed at wound drain, catheter, and ostomy entry sites. In further aspects of the invention, copper salts of ion exchange materials may be used to carry out methods of killing microorganisms, and may optionally be used in conjunction with additional anti-infective agents.

2. Description of Related Art

Surgical Site Infections (SSIs) account for approximately 500,000 nosocomial infections each year an added cost of more than $3,000 per infection, with a total impact on the healthcare system being over $1.5 billion per year. The post operative infection rates for surgical procedures averages between 2% to 4% for all procedures with selected procedures having significantly higher rates. The surgical procedures associated with the highest rates of infection and morbidity include coronary artery bypass graft (CABG), cardiac surgery, colon surgery, hip arthroplasty, knee arthroplasty, hysterectomy, thromboendarterectomy, and vein bypass.

In addition, approximately 30% of patients undergoing hemodialysis have permanent central line catheters (CLSs), and these patients experience insertion site and bloodstream infections (BSIs) at high rates. Other indwelling catheters are also associated with high rates of infection.

A number of approaches have been developed in an attempt to address the problem of infections in wounds, such as wounds formed by surgical procedures, lacerations, abrasions, burns, as well as long-term or chronic wounds such as those formed at wound drain sites, catheter entry sites, and ostomy exit sites. Anti-infective agents, including antimicrobial agents, antibiotics, antifungals, and antivirals, have been incorporated into a variety of wound care products such as wound dressings, bandages, creams, and ointments.

Several metals are known to possess antimicrobial properties, including silver, copper, lead, cadmium, palladium, and zinc. Of these, copper has the advantage of being a naturally-occurring ion found in the human body. Copper is found in human plasma in concentrations of about 0.85 ug/ml+/−0.19, and its presence in the body is known to be tolerated for long periods of time, as evidenced by the use of medical devices such as the copper-coated IUD.

UK Patent Application No. GB 2 092 006 describes a germicidal wound or burn dressing including an absorbent pad and a non-absorbent liquid-permeable sheet that is coated with metallic copper or a copper compound. The copper-containing sheet is placed in contact with the wound or burn, and protects against bacteria without causing the bacteria to develop resistance.

U.S. Pat. No. 4,637,820 describes a modified fibrous material comprising cellulose fibers that are substituted at their cellulose anhydroglucose units with anionic moieties, and capped by copper cations such that the fibers bind from about 0.1% by weight to about 3.0% by weight of copper based on the weight of the fibers. Methods of preparing a copper-modified carboxyalkyl cellulose fiber are also described, which include treating the fibers with an aqueous cupric salt solution and washing the fibers to remove the salt, followed by drying. The fibers preferably have a degree of copper substitution of from 0.01 to 0.3. Materials prepared using the fibers may include surgical dressings, absorbent cotton, and various hygienic devices.

U.S. Pat. No. 5,977,428 describes absorbent dressings for absorbing exudates from wounds, where the dressings contain a plurality of absorbent hydrogel particles sealed within a porous container. The porous container does not adhere to the wound, and the hydrogel particles remain sealed in the container after absorbing the exudate. The particles may be dried polyacrylonitrile hydrogel particles, and the particles may contain or release wound healing agents or nutrients that aid the healing process, such as copper- and zinc-containing compounds or complexes.

PCT Published Application No. WO 2008/101417 describes a hydrogel dressing for covering or treating a wound, and methods for preparing such dressings. The dressing includes a matrix structure including a cross-linked mixture, and an elastic sheet coated with an elemental metal or an ionic metal that is embedded in the matrix structure. The cross-linked mixture comprises a hydrophilic polymer, a photocatalyst, and water. The metal is preferably. $TiO_2$ in combination with silver ions, although zinc and copper may also be used in place of the silver.

U.S. Published Application No. 2008/0311165 describes methods for treating and healing sores, cold sores, cutaneous openings, ulcers, lesions, abrasions, burns, and skin conditions by applying a polyamide, polyester, acrylic, or polyalkylene material having water-insoluble copper oxides embedded therein. The material releases copper (I) ions, copper (II) ions, or combinations thereof upon contact with a fluid.

Current anti-infective dressings available on the market incorporate silver as an anti-infective agent. These dressings are expensive (about 5-10 times more expensive than conventional dressings), and are therefore are only used for severe burns, chronic non-healing wounds, and in high-risk patients. Exemplary dressings include Argentum Medical's Silverlon® dressing, Johnson & Johnson's Acticote® dressing, Medline's Argalase® dressing, Smith & Nephew's Actisorb® dressing, and Conoplast's Contreed® dressing.

Although there are a variety of silver-based products available on the market, the high prices associated with these dressings deters their use in many situations where they might be helpful in preventing infections. Further, although silver and other metals such as lead, palladium, cadmium, and zinc can be effective as antimicrobial agents, these metals can accumulate in the body and are not easily eliminated, which can be detrimental to the healing process.

There is a need in the art for cost-effective anti-infective products. There is also a need for articles of manufacture that provide anti-infective properties by releasing copper ions in a controlled, consistent manner when contacted with fluids, such as water, perspiration, and wound exudates. Such articles may incorporate copper salts of ion exchange resins, where the articles may be in the form of, e.g., wound dressings, gauzes, bandages, and/or topical preparations in the form of creams, gels, hydrogels, and ointments. The articles that release copper ions may produce an equilibrium of copper ions in a wound at a level that is therapeutically-effective for preventing infection. Further, the anti-infective products in accordance with the present invention provide a cost-effective alternative to currently-available silver-based anti-infective dressings, thereby broadening the number of applications for which the anti-infective dressings of the present invention may be used.

SUMMARY OF THE INVENTION

The present invention meets the unmet needs of the art, as well as others, by providing anti-infective copper delivery systems that provide consistent, controlled release of copper ions upon contact with fluids. The copper ions are released at levels that are suitable for use in biological systems, preferably by establishing an equilibrium of the copper ions in a fluid at a level that is therapeutically-effective for preventing infection, yet does not exceed toxic levels.

The copper delivery system may beneficially be provided in the form of copper salts of ion exchange resins such as cellulose derivatives, including ether and ester derivatives of cellulose. Presently preferred cellulose derivatives include carboxymethyl cellulose (CMC), ethylcellulose (EC), methylcellulose (MC), hydroxypropyl cellulose (HPC), hydroxypropyl methyl cellulose (HPMC), hydroxyethyl methyl cellulose (HEMC), cellulose acetate, cellulose triacetate, and salts thereof. According to one aspect, CMC, sodium-CMC, and calcium-CMC may be used as the ion exchange resin. According to further aspects, the copper salts of ion exchange resins may be used to prepare a hydrocolloid capable of absorbing fluids.

The invention also provides articles, such as wound dressings, gauzes, bandages, and/or topical preparations in the form of creams, gels, hydrogels, and ointments, where the articles incorporate copper salts in a form suitable for establishing an equilibrium of copper ions. This invention also provides methods for preventing infections in wounds, including long-term, non-healing, and chronic wounds. For example, the articles containing copper salts may be used in methods of reducing the incidence of infection in wounds such as surgical wounds, lacerations, abrasions, and burns, as well as long-term wounds, such as ulcers, and wounds formed at wound drain, catheter, and ostomy sites. The present invention is further directed towards methods of making articles, such as wound dressings, gauzes, bandages, and/or topical preparations in the form of creams, gels, hydrogels, and ointments, which incorporate the copper salts.

According to one aspect of the invention, the invention relates to copper salts of ion exchange resins. The ion exchange resins may be cellulose derivatives selected from the group consisting of carboxymethyl cellulose (CMC), ethylcellulose (EC), methylcellulose (MC), hydroxypropyl cellulose (HPC), hydroxypropyl methyl cellulose (HPMC), hydroxyethyl methyl cellulose (HEMC), cellulose acetate, and cellulose triacetate. The copper salts may be formed from copper (I) and/or copper (II) ions. Upon contact with liquids such as water, perspiration, and wound exudates, the copper salts may beneficially produce an equilibrium of copper ions in the liquid at a level that is therapeutically-effective for preventing infection.

According to one aspect of the invention, articles are provided that incorporate copper salts of ion exchange resins. The ion exchange resins may be formed from cellulose derivatives selected from the group consisting of carboxymethyl cellulose (CMC), ethylcellulose (EC), methylcellulose (MC), hydroxypropyl cellulose (HPC), hydroxypropyl methyl cellulose (HPMC), hydroxyethyl methyl cellulose (HEMC), cellulose acetate, and cellulose triacetate. The articles may be provided in the form of wound dressings, gauzes, bandages, creams, gels, hydrogels, and ointments.

An additional aspect of the invention relates to a method of preparing anti-infective wound care articles. The method includes providing an ion exchange material, providing a solution of one or more copper salts, soaking said ion exchange material in said solution of one or more copper salts, and removing the solvent to form a copper salt of said ion exchange material. The copper salt of cellulose derivatives may be beneficially incorporated into articles such as wound dressings, gauzes, bandages, creams, gels, hydrogels, and ointments.

Yet another aspect of the invention relates to a method of providing an anti-infective agent at a wound site, comprising forming an article incorporating copper salts of ion exchange materials, applying the article to a wound site, and allowing liquid from the wound site to contact the article, wherein an equilibrium is attained between copper ions in the fluid from the wound site and copper ions associated with the copper salts of the ion exchange materials in the article.

A further aspect of the invention relates to a method for treating an infection, comprising applying an article incorporating copper salts of ion exchange materials to an infected wound. The infected wound may be a long-term, non-healing, and/or chronic wound. The methods of treating infection may also be used to reduce the incidence of infection of a wound, by applying articles incorporating copper salts of ion exchange materials to wounds, and comparing the rate of infection in said wounds to the rate of infection in wounds not treated using articles containing copper salts of ion exchange materials. The wounds may be selected from the group consisting of surgical wounds, lacerations, abrasions, burns, skin ulcers, wound drains, catheter sites, and ostomy sites.

Other novel features and advantages of the present invention will become apparent to those skilled in the art upon examination of the following or upon learning by practice of the invention.

BRIEF DESCRIPTION OF THE DRAWINGS

Aspects of the present invention will become fully understood from the detailed description given herein below and the accompanying drawings, which are given by way of illustration and example only.

DETAILED DESCRIPTION OF THE PREFERRED EMBODIMENTS

Figure 1:
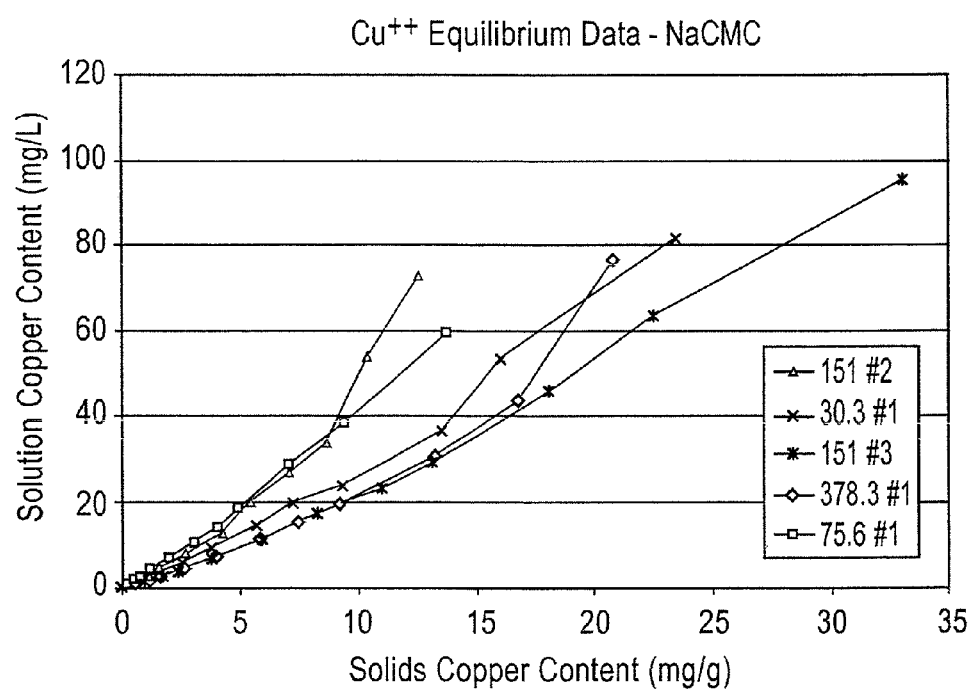
FIG. 1 is a graph showing the effect of Na+ CMC solids Cu++ content on dissolved Cu++ content.

The copper delivery systems for use in the present invention may be used to establish an ion exchange equilibrium in which copper ions are released into a biological fluid at non-toxic levels that are sufficient to provide an antimicrobial effect. According to some aspects, the copper delivery systems may be salts of positively-charged copper (I) and/or copper (II) cations, and negatively charged anions of any substance that is capable of releasing the copper cations in a controlled, consistent manner upon contact with a fluid.

According to some aspects, the anions are formed from ion exchange resins. According to further aspects, the ion exchange resin may be a cellulose derivative. The anionic substances may include, without limitation, ether and ester derivatives of cellulose, including carboxymethyl cellulose (CMC), ethylcellulose (EC), methylcellulose (MC), hydroxypropyl cellulose (HPC), hydroxypropyl methyl cellulose (HPMC), hydroxyethyl methyl cellulose (HEMC), cellulose acetate, and cellulose triacetate. According to a presently preferred embodiment, the ion exchange resin is CMC, preferably sodium-CMC and/or calcium-CMC. Regardless of the particular anion used, the copper delivery systems of the invention release copper cations in an amount that provides an antimicrobial effect.

The copper delivery systems may be prepared by adding a concentrated solution of soluble copper salts (e.g., copper sulfate, copper chloride) into an aqueous solution of an ion exchange resin, such as CMC, which may be provided in the form of sodium CMC and/or calcium CMC. According to some aspects of the invention, the CMC has a degree of substitution that is less than 0.95, preferably less than 0.70. The copper salts of CMC may then be filtered and purified to remove unbound copper, and then dried to form the final product.

According to some aspects, when the ion exchange resin is CMC, the resin preferably has a degree of copper substitution of from about 0.001 to about 0.5, more preferably 0.01 to about 0.3. The total amount of copper provided in the copper delivery systems is preferably from about 0.0001% by weight to about 0.0005% by weight, more preferably from about 0.0002% by weight to about 0.0004% by weight, and most preferably about 0.0003% by weight. The appropriate amounts of copper contained in copper salts of different ion exchange resins can be calculated by one skilled in the art based on the levels given above for the copper-CMC salts. Although the copper ions will replace other ions, such as sodium and/or calcium, the degree to which the copper replaces those ions will typically be about 50% or less, preferably 35% or less, more preferably 20% or less, and most preferably 10% or less based on the degree of substitution of the CMC or other cellulose derivative.

Regardless of the particular ion exchange resin used and its degree of substitution, the amount of copper contained in the copper delivery system is selected such that there is enough copper present to exchange with sodium, calcium, or other cations present in a fluid while providing the copper cations in an effective amount, without causing the concentration of copper ions to build to levels that cause irritation. Preferably the amount of copper is sufficient to exchange with sodium, calcium, or other cations present in the serum of an animal in order to provide copper cations in an amount that is antimicrobially-effective, without causing the concentration of copper ions to build up to a level that causes systemic toxicity in the animal. By providing a controlled ion exchange, therapeutic levels of copper ions are attained in the serum of an animal, such that the copper delivery systems beneficially treat and/or prevent infections caused by infective agents such as bacteria, viruses, and fungi.

The copper salts of ion exchange resins, such as cellulose derivatives, may be incorporated into a variety of medical articles in order to provide the articles with anti-infective properties.

Wound care products that may beneficially incorporate the copper salts of ion exchange resins of the present invention include any wound dressings, bandages, gauzes, ointments, powders, creams, gels, and/or hydrogels that may be used in conjunction with the treatment of surgical wounds, lacerations, abrasions, burns, chronic or non-healing wounds (i.e., ulcers), wound drain insertion sites, catheters, and ostomy sites.

The wound care and wound infection prevention articles can be formed of any materials that are suitable for use in wound treatment and/or infection prevention, and are compatible with the copper salts of ion exchange resins. The articles of the present invention may be formed from essentially any material that is capable of maintaining an association with the copper salts of ion exchange resins, and that allows for release of copper ions. According to some aspects, the wound care and wound infection prevention articles may be used in conjunction with methods for reducing and/or eliminating the use of antibiotics at a surgical site or on a wound, thereby reducing costs while providing a complete spectrum of antimicrobial effectiveness that simultaneously reduces the potential for antibiotic resistance.

The incorporation of copper salts of ion exchange resins, such as cellulose derivatives, into the articles of the present invention may follow one of two approaches: (1) providing a layer containing the copper salts of ion exchange resins on the article; or (2) incorporating the copper salts of ion exchange resins into the articles. According to some aspects of the invention, the copper salts of ion exchange resins may provide a sustained release of the copper ions by establishing an equilibrium between the copper ions found in the copper salts of ion exchange resins and the copper ions in the fluid surrounding the wound. Establishing such an equilibrium may beneficially provide long-term anti-infective efficacy. According to other aspects of the invention, the copper salts of ion exchange resins may provide a rapid initial release of the copper ions until an equilibrium is established, in order to provide a quick kill of any bacteria, viruses, and/or fungi in or around the wound.

According to one aspect, the wound care articles are hydrocolloid adhesive systems, where the hydrocolloid incorporates a copper salt of an ion exchange resin, for example, a CMC-copper salt, in an amount of from 0.5% to 5% by weight of the hydrocolloid, preferably from 0.75% to 4% by weight, more preferably from 1% to 3% by weight. The hydrocolloid adhesive system is prepared by providing a hydrocolloid containing a copper salt, which is then blended and extruded. The blended hydrocolloid adhesive containing a copper salt is then provided in a finished hydrocolloid wound dressing using manufacturing techniques known to those skilled in the art. Such wound dressings may be prepared in a variety of sizes and shapes for use in treating a variety of wounds that may occur on different body surfaces.

In accordance with additional aspects of the present invention, the copper salts may also be incorporated into medical adhesives, such as pressure sensitive adhesives, or they may be provided in medical incise drape formulations. When used in conjunction with these aspects of the invention, the copper salts are able to release copper ions into surgical wound sites in a controlled manner as the procedure is being performed, in order to reduce the incidence of infection typically associated with the surgical procedure.

It is considered within the ability of those skilled in the art to prepare alternative wound care articles, such as powders, creams, and bandages, that provide anti-infective amounts of copper ions using the guidance provided above.

The copper salts of ion exchange resins are preferably included in or on the articles in amounts that are effective for reducing the amount of microbes in or around the wound. According to a further aspect, the copper salts of ion exchange resins are provided in amounts that are effective for eliminating all microbes in or around the wound. In particular, the copper salts of ion exchange resins are provided in amounts that release microbicidally- or microbistatically-effective amounts of copper ions, while not being toxic to the patient.

The concentration of copper salts of ion exchange resins necessary to achieve the desired effect will vary based on factors including, but not limited to, the context in which the article is used (i.e., type of wound, and amount of moisture associated with the wound environment), the manner in which the copper salts of ion exchange resins are incorporated into the article (i.e., as a coating, or embedded within the article), and the types of microbes that are associated with the wound environment.

The concentration of copper ions released into the wound environment due to the equilibrium established between the copper salts of ion exchange resins in the articles and the fluid present in the wound environment will vary based on the amount of copper salts of ion exchange resins provided in or on the article, and the amount of cations present in the fluid associated with the wound. Where inadequate levels of fluid and/or cations are present in the wound environment, they may be supplemented by wetting the article with a sterile liquid (when the article is in the form of a surgical dressing, gauze, or bandage), or by using the copper salts of an ion exchange resin in conjunction with an article that contains a source of moisture and/or cations (such as a gel, hydrogel, or cream containing the copper salts of cellulose derivatives).

Preferably the copper salts of ion exchange resins, such as cellulose derivatives, are included in or on the articles of the present invention in amounts that are adequate to release concentrations of copper ions that kill or restrict the growth of one or more of the following microbes: coagulase-negative Staphylococci, Enterococci, fungi, *Candida albicans, Staphylococcus aureus, Enterobacter species, Enterococcus faecalis, Staphylococcus epidermidis, Streptococcus viridans, Escherichia coli, Klebsiella pneumoniae, Proteus mirabilis, Pseudomonas aeruginosa, Acinetobacter baumannii, Burkholderia cepacia, Varicella, Clostridium difficile, Clostridium sordellii,* Hepatitis A, Hepatitis B, Hepatitis C, HIV/AIDS, methicillin-resistant *Staphylococcus aureus* (MRSA), mumps, norovirus, parvovirus, poliovirus, rubella, SARS, *S. pneumoniae* (including drug resistant forms), vancomycin-intermediate *Staphylococcus aureus* (VISA), vancomycin-resistant *Staphylococcus aureus* (VRSA), and vancomycin-resistant *Enterococci* (VRE). It is considered to be within the ability of one skilled in the art to determine such amounts.

The present invention may also be used in accordance with methods of preventing infections, reducing the incidence of infections, and/or treating existing infections in wounds. Such methods include providing an article, and incorporating copper salts of ion exchange resins therein or thereon in an amount sufficient to provide a concentration of copper ions sufficient to kill or suppress the growth of any microorganisms that are found in the area surrounding the article. The concentration of copper salts that will be required to establish a suitable concentration of copper ions in the wound will vary based on the size of the wound, whether the wound is already infected, and the microorganisms that are present in the vicinity of the wound.

These and other aspects of the invention are further described in the non-limiting Examples set forth below.

EXAMPLES

Example 1

Preparation of Copper Salts of CMC

Approach:

The mixed cupric/sodium and cupric/calcium salts of carboxymethylcellulose (CMC) are prepared by precipitation by pipetting concentrated solutions of copper salts into a aqueous solutions of sodium carboxymethylcellulose and calcium carboxymethylcellulose. The copper salts are prepared either from USP copper sulfate or reagent grade copper chloride. The salts are isolated by filtration and subsequently purified by displacement washings with aqueous methanol and then dried in vacuo.

Reagents Required:

USP sodium carboxymethylcellulose. Calcium carboxymethycellulose. The CMC should be a degree of substitution less than or equal to 0.95, preferably about 0.70, and be a medium viscosity type; distilled water; anhydrous methanol; sodium chloride; $CuSO_4.5H_2O$ (for copper salt), USP grade and copper chloride Reagent Grade.

Apparatus Required:

Overhead stirrer; 500 ml beakers; 1 liter 3-necked, round bottomed flask; 500 ml 3-necked round bottomed flask; vacuum oven set to 75° C.; small crystallizing dish; source of vacuum (pump and aspirator); 1 liter filter flask with 2-3" Buechner funnel and coarse filter paper to fit or a funnel with a sintered glass frit; analytical balance, good to 0.1 g; plastic weighing dishes; brown glass bottles; 100 ml, 250 ml and 500 ml graduated cylinders; magnetic stirrer and stirring bars; 250 ml 1-necked round-bottomed flasks; rotary evaporator; burette, spatulas, clamps as needed.

Synthesis Procedure for Mixed Copper/Sodium Salt of CMC:

1. Prepare 400 ml of a saturated cupric sulfate pentahydrate solution. Alternatively a saturated solution of cupric chloride may be used.

2. Place approximately 3 ml of the CMC (weighed to 0.1 g) solution into a small beaker and add the cupric sulfate pentahydrate solution drop wise via burette. Observe the formation of any precipitate. If there is a precipitate, allow the precipitate to settle and add one more drop of cupric sulfate pentahydrate solution to assure that precipitation is complete. Record the amount of copper solution added and proceed to step 3.

3. Place 200 g of the sodium or calcium carboxymethylcellulose solution into a 1 liter round-bottomed flask. Agitate gently with overhead stirrer. Slowly add by burette the amount of cupric sulfate pentahydrate solution calculated from step 2 to effect precipitation of the product. Stir for 15 minutes following addition to assure complete precipitation.

4. Carefully filter the aqueous solution from the precipitate. Weigh and retain for analysis. Place the precipitate into a 500 ml beaker.

5. Prepare a solution of 360 ml of methanol and 240 ml of deionized water.

6. Suspend the precipitate in 100 ml of aqueous methanol in the beaker, stir for 10 minutes. Decant the liquid as well as possible into a tared flask and re-suspend in 100 ml of the methanol. Stir again for 10 minutes. Evaporate the aqueous methanol solutions separately and determine weight of any residue. If there is visible residue, capture it for analysis.

7. Isolate the precipitate on the funnel once again and wash with a small amount of aqueous methanol. Once again evaporate in a tared round-bottom flask and retain any residue for analysis after weighing.

8. Re-suspend the precipitate in 100 ml of the aqueous methanol. Stir for 10 minutes and filter again, saving the filtrate. Dissolve 0.1 g sodium carbonate in 1 ml of distilled water and add three drops to the filtrate. If the filtrate is clear, go to step 9. If not, repeat step 8 until it is clear. A clear solution indicates that all the remaining copper is present as the CMC salt.

9. When the filtrate is clean of uncombined copper ion, carefully transfer the precipitate to a plastic weighing dish. Place the dish in the vacuum oven and dry at 105° C. Weigh dry powder and store dry Cu/Na CMC in a capped brown glass bottle until use.

10. Do a material balance on the process, accounting for the Na and copper salt in the process. From the analysis, calculate the Cu degree of substitution in the product.

Example 2 (Comparative)

Preparation of Silver Salts of CMC

Approach:

The silver/sodium salts of carboxymethylcellulose (CMC) are prepared by precipitation by pipetting concentrated solutions of soluble silver salts into aqueous solutions of sodium carboxymethylcellulose. The silver salt is prepared form either from USP silver nitrate. The salts are isolated by filtration and subsequently purified by displacement washings with aqueous methanol and then dried in vacuo.

Reagents Required:

USP sodium carboxymethylcellulose. The CMC should be a degree of substitution less than or equal to 0.95, preferably about 0.70, and be a medium viscosity type; silver nitrate, USP grade; distilled water; anhydrous methanol; sodium chloride.

Apparatus Required:

Overhead stirrer; 500 ml beakers; 1 liter 3-necked, round bottomed flask; 500 ml 3-necked round bottomed flask; vacuum oven set to 75° C.; small crystallizing dish; source of vacuum (pump and aspirator); 1 liter filter flask with 2-3" Buechner funnel and coarse filter paper to fit or a funnel with a sintered glass frit; analytical balance, good to 0.1 g; plastic weighing dishes; brown glass bottles; 100 ml, 250 ml and 500 ml graduated cylinders; magnetic stirrer and stirring bars; 250 ml 1-necked round-bottomed flasks; rotary evaporator; burette, spatulas, clamps as needed.

Synthesis Procedure for Mixed Silver/Sodium Salt of CMC:

1. Prepare 400 g of 50% w/w aqueous silver nitrate in deionized water. Store in a brown glass bottle if not used at once.

2. Place approximately 3 ml of the CMC (weighed to 0.1 g) solution into a small beaker and add the silver nitrate solution drop wise via burette. Observe the formation of any precipitate. If there is a precipitate, allow the precipitate to settle and add one more drop of silver nitrate solution to assure that precipitation is complete. Record the amount of silver solution added and proceed to step 3.

3. Place 200 g of the sodium carboxymethylcellulose solution into a 1 liter round-bottomed flask. Agitate gently with overhead stirrer. Slowly add by burette the amount of silver nitrate calculated from step 2 to effect precipitation of the product. Stir for 15 minutes following addition to assure complete precipitation.

4. Carefully filter the aqueous solution from the precipitate. Weigh and retain for analysis. Place the precipitate into a 500 ml beaker.

5. Prepare a solution of 360 ml of methanol and 240 ml of deionized water.

6. Suspend the precipitate in 100 ml of aqueous methanol in the beaker, stir for 10 minutes. Decant the liquid as well as possible into a tared flask and re-suspend in 100 ml of the methanol. Stir again for 10 minutes. Evaporate the aqueous methanol solutions separately and determine weight of any residue. If there is visible residue, capture it for analysis.

7. Isolate the precipitate on the funnel once again and wash with a small amount of aqueous methanol. Once again evaporate in a tared round-bottom flask and retain any residue for analysis after weighing.

8. Re-suspend the precipitate in 100 ml of the aqueous methanol. Stir for 10 minutes and filter again, saving the filtrate. Dissolve 0.1 g sodium chloride in 1 ml of distilled water and add three drops to the filtrate. If the filtrate is clear, go to step 9. If not, repeat step 8 until it is clear. A clear solution indicates that all the remaining silver is present as the CMC salt.

9. When the filtrate is clean of uncombined silver ion, carefully transfer the precipitate to a plastic weighing dish. Place the dish in the vacuum oven and dry at 105° F. for one hour. Weigh dry powder and store dried Ag/Na CMC in a capped brown glass bottle until used.

10. Do a material balance on the process, accounting for the Na CMC and the silver salt used in the process. From the analysis, calculate the Na and Ag salt degrees of substitution in the reaction product.

Example 3

Evaluation of Equilibrium Levels of Copper and Silver Cations

Product Characterization—Sample Digestion:

Transfer an accurately weighed sample containing 20-30 mg. silver or 10-15 mg. copper to a borosilicate digestion flask. Add 5 ml. ACS Reagent Grade sulfuric acid to the sample and swirl it to wet the sample. Then add 1.0 ml. ACS Reagent Grade nitric acid with swirling to mix. Heat the flask in a fume hood to start the digestion. Then heat the flask to fumes of sulfuric acid. If the solution is clear continue heating to reduce the amount of sulfuric acid to less than 2 ml. If there is a black residue at the end of the first heating, allow the flask to cool and then add carefully 1.0 ml. of nitric acid and repeat the heating to fumes. Repeat as necessary to finish oxidizing the carbon residue. Let the flask cool to room temperature and then add 25 ml. deionized water to the flask with swirling to mix the water with the acid. Warm to dissolve the salts if necessary. Then transfer to the titration vessel and prepare for titration.

If the ISE technology is to be used for the determination of the metals the sample size may be reduced by about 10 fold so that there will be 2-3 mg. silver or 1-2 mg copper. The accurately weighed sample may be transferred to 30 mm×120 mm borosilicate test tube for the digestion. The sulfuric acid added should be reduced to 1.0 ml. and the nitric acid be reduced to 0.5 ml. Heat to strong fumes of sulfuric acid. If any dark residue remains, add 0.5 ml more nitric acid and heat to provide a clear digest. The final volume of the digest should be less than 0.5 ml. The digest should be carefully diluted with deionized water and transferred to the analysis vessel for the final determination.

Product Characterization—Determination by Titration:

Silver: Add a drop of methyl orange indicator to the sample solution and add 1N NaOH to the intermediate color of the methyl orange. Dilute with deionized water to 60 to 75 ml. with deionized water. Place on the titration stand and titrate with 0.050 M KCl solution. The titrator will be equipped with a 10 ml. or 20 ml. burette and use a silver sensing electrode in combination with a standard double junction reference electrode. The reference electrode will contain 1 M potassium nitrate as specified by the vendor. Standard vendor supplied titrator protocol will be used and the results and the titration curve will be printed for the record. A precisely measured volume of standard silver nitrate solution will be used as a QC standard.

Copper: The procedure is essentially the same except that the silver sensing electrode is replaced with a copper ISE electrode and the titrant used is 0.050 N EDTA solution. Adjust the pH of the solution to 7-8 with ACS Reagent Grade ammonium hydroxide. Dilute to 60-75 ml. with deionized water. If calcium, magnesium or zinc are suspected the pH should be adjusted to 3.8-4.2 with 2M sodium acetate solution rather than with ammonium hydroxide. The EDTA solution is standardized with, standard copper solution, or alternately with a standard zinc solution. These standards may be purchased or prepared from the pure metals.

Alternative Determination by Ion Selective Electrode:

Silver Electrode Calibration:

Determine the electrode response over the range, 0.1 to 20 mg. silver per liter, in a buffer solution containing 0.1 M sodium acetate/0.1 M acetic acid. Use a standard solution of silver nitrate prepared from ACS Reagent Grade silver nitrate and deionized water. Calculate the slope of the plot of the log [Ag] vs. the mV measured. The slope should be between 56 and 61 mV per 10 fold change in the silver concentration. It will be used in the calculation of the silver content of the acid digest.

Silver Sample Analysis:

Add two drops methyl red indicator solution to the sample and add 50 ml. deionized water. Then add 2M sodium acetate solution to the sample solution until the solution turns from red to orange. Add deionized water to dilute the sample to 200 ml. immerse the electrode set in the solution and stir slowly. Record the mV reading when it stabilizes. Refer to the electrode calibration plot to estimate the concentration of silver in the solution. Add a measured volume of silver nitrate solution to the sample solution to provide a change of 12 to 24 mv. A reasonable estimate is a volume required to increase the silver concentration in the solution 60% to 150% of the original concentration. Record the volume added and the mV reading. Add another increment of silver nitrate of the same volume to the solution and record the volume added and the mV reading. Refer to the vendor's electrode manual for the calculation.

Copper Electrode Calibration:

Determine the electrode response over the range, 0.1 to 20 mg. copper per liter, in a buffer solution containing 0.1 M sodium acetate/0.1 M acetic acid. Use a standard solution of copper chloride prepared from ACS Reagent Grade copper chloride pentahydrate and deionized water. Calculate the slope of the plot of the log [Cu] vs. the mV measured. The slope should be between 28 and 31 mV per 10 fold change in the copper concentration. It will be used in the calculation of the copper content, of the acid digest.

Copper Sample Analysis:

Add two drops methyl red indicator solution to the sample and add 50 ml. deionized water. Then add 2M sodium acetate solution to the sample solution until the solution turns from red to orange. Add deionized water to dilute the sample to 200 ml. Immerse the electrode set in the solution and stir slowly. Record the mV reading when it stabilizes. Refer to the electrode calibration plot to estimate the concentration of copper in the solution. Add a measured volume of copper chloride solution to the sample solution to provide a change of 10 to 18 mv. A reasonable estimate is a volume required to increase the copper concentration in the solution 2.3 to 4.0 times the original concentration. Record the volume added and the mV reading. Add another increment of copper chloride solution of the same volume to the solution and record the volume added and the mV reading. Refer to the vendor's electrode manual for the calculation.

Ion Exchange/Solubility Studies:

The copper and silver ion selective electrodes can be used to monitor the total dissolved species in aqueous metal complexing solutions such as Ringer's lactate. The electrodes respond to the free ion only but the ratio of the concentration of it to the total dissolved ions remains constant as long as the concentration of the complexing agent remains essentially constant. If the metal ion is precipitated as happens with silver ion in Ringer's lactate solution the electrode will not provide information on the silver present as silver chloride. However, complexing agents such as ammonia can be used in sample preparation to avoid acid digestion to prepare the sample for analysis by ISE technology. The standard addition technique is required when this kind of approach is used for sample preparation.

It is planned to use the ISE direct reading technology to monitor the rate of solubility of the silver and copper compounds prepared in this program. It will provide information on the concentration of the free metal ions and when the solution has reached saturation. It is expected that the high chloride concentration in the Ringer's lactate solution will precipitate silver chloride when the silver CMC salt is stirred with the solid. If this appears to be a significant fate of the silver CMC salt it may be appropriate to determine the silver content of the solid isolated from the equilibration solution.

The total solubility of the silver and copper in the respective solutions will be measured by ISE after sample preparation. The sample preparation will include filtration to remove the suspended solids and acid digestion as described in the analysis of the products. Analysis by treatment of the filtered solution with ACS Reagent Grade ammonium hydroxide followed by ISE standard addition technology will be tested as an alternate to the acid digestion method. If the results are equivalent, the ammonium hydroxide sample preparation will be used. The titration method for copper and silver require larger samples than would ordinarily be available. The larger samples required for titration would take a great deal more time to prepare than the sample size required for ISE analytical methods.

Analytical Methods:

Analysis of the prepared samples was done using a Sulfuric Acid Digestion followed by an EDTA Titration monitored by a Cu++ Ion Specific Electrode. Samples prepared from Ca++ CMC had to be titrated at less that pH 5 to eliminate the Calcium Interference. Overall the ISE methodology showed excellent promise.

On each day of experimental analysis, the Ion Specific Electrode was calibrated by the Method of Standard Additions to assure accurate measurements. In addition, Methods of Additions trials were performed against the various ionic solutions (salt background, digestion acid solutions, Lactated Ringers, etc.) to assure accurate electrode performance. All the dispensing pipettes used in the analytical programs were also calibrated.

During the equilibrium studies using Ringers Lactate as the ionic solution, it was noted that the Ringers Lactate caused a significant shift in the intercept of the electrode readings. This is likely caused by the formation of lactate complex of the free Cu++ ions. This suggests that future development should use ionic solutions containing inorganic salts only; this will simplify the interpretation of the experimental data.

Time to Equilibrium Studies:

Samples of the Cu++ CMC materials were agitated in 150 ml of Lactated Ringers Solution. The expression of the Cu++ ion from the salts was measured using Cu++ Ion Specific Electrode. The goal of these trials was to understand approximately how fast the Cu++ could be ion exchanged off of the Cu++ CMC salt. The data from these trials indicates that these salts equilibrate very quickly in the Lactated Ringers; usually within five, minutes for the Na+ CMC based materials and within seven minutes for the Ca++ CMC based materials.

This data is strongly encouraging as it indicates that these Cu CMC materials would quickly and freely liberate their attached Cu++ ions into a competing ion exchange medium such as wound fluid. Further, replicates of the experiments indicate that the final equilibriums reached for two of the synthesized materials were very consistent.

Cu++CMC Equilibrium Studies:

Ion exchange equilibrium studies were conducted using both Ca++ CMC and Na+ CMC.

The procedure consisted of adding a small amount a CMC reagent (less than 1.5 grams of Ca++ CMC or less than 0.5 grams of Na+ CMC) of to Ringers Lactate (100 ml-300 ml). The Ringers Lactate was used as the source of cations for the Cu++ ion exchange. This mixture was agitated in a beaker using a stirring bar. Standard additions of CuCl2 were added to the agitated mixture and the dissolved copper monitored using as Cu++ Ion Specific Electrode.

Figure 2:
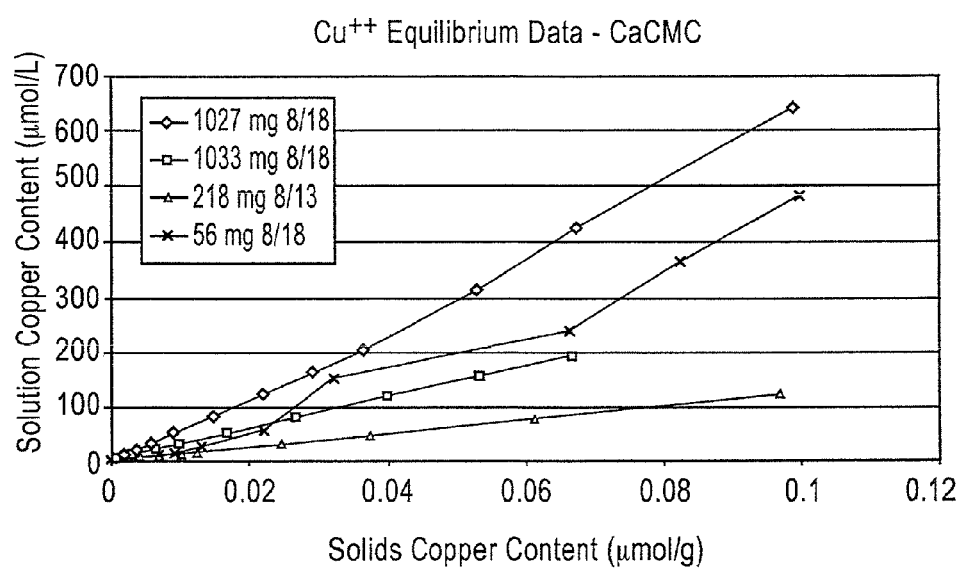
FIG. 2 is a graph showing the effect of Ca+ CMC solids Cu++ content on dissolved Cu++ content.

Data showing the dissolved Cu++ content vs. the Na+ CMC Solids Cu++ content is included in Tables 1-5, and is plotted in FIG. 1. Data showing the dissolved Cu++ content vs. the Ca++ CMC Solids Cu++ content is included in Tables 6-9, and is plotted in FIG. 2. While the essentially straight line plots indicate that these materials exhibit typical ion exchange agent behavior; the different slopes of the lines indicate that there may have been some competing factor that was not held constant during the testing. In the future, it is suggested to not use Lactated Ringers Solution as the ion exchange medium, as the lactate component has been shown to complex with the Cu++ ion and render it unreadable by the specific ion electrode. It is also recommended that higher ratios of solids/liquids be used to better represent the proposed product use environments.

Finally, in future laboratory trials, the relationship of particle size of the CMC reagents to the consistency of the experimental data obtained will be investigated.

TABLE 1

Add 20.0 ml. Na+ CMC solution to 130 ml.
Lactated Ringers solution (151.3 mg. Solid)
Sep. 29, 2004

| Cu, mg./l. | Copper mg./l. | Solids-Cu mg/g |
|---|---|---|
| 0 | | |
| 0.214533 | 0.217568 | −0.00301 |
| 0.429067 | 0.345369 | 0.083144 |
| 0.858013 | 0.565393 | 0.290682 |
| 1.2872 | 0.850404 | 0.433903 |
| 2.145333 | 1.319104 | 0.820757 |
| 4.295386 | 2.597897 | 1.686247 |
| 6.445439 | 3.998812 | 2.430424 |
| 10.75799 | 6.908952 | 3.823548 |
| 17.18326 | 11.31044 | 5.833927 |
| 25.65561 | 17.4096 | 8.191401 |
| 34.12796 | 23.14976 | 10.9055 |
| 42.60031 | 29.39243 | 13.12041 |
| 64.09226 | 45.94456 | 18.02752 |
| 85.58421 | 63.00443 | 22.43025 |
| 128.7054 | 95.49717 | 32.98831 |

TABLE 2

Add 20.0 ml. Na+ CMC solution to 130 ml.
Lactated Ringers solution (151.3 mg. Solid)
Sep. 17, 2004

| Cu, mg./l | Cu, mg./l. | Solids-Cu mg/g |
|---|---|---|
| 0.214533 | 0.142784 | 0.071133 |
| 0.429067 | 0.257708 | 0.169887 |
| 0.858133 | 0.519333 | 0.335889 |
| 1.2872 | 0.782077 | 0.500783 |
| 2.145333 | 1.325387 | 0.812901 |
| 4.295386 | 3.277649 | 1.008992 |
| 6.445439 | 4.858784 | 1.573022 |
| 10.75799 | 8.041979 | 2.692674 |
| 17.18326 | 12.99991 | 4.147406 |
| 25.65561 | 20.20325 | 5.405512 |
| 34.12796 | 27.03557 | 7.031451 |
| 42.60031 | 33.96998 | 8.556176 |
| 64.09226 | 53.63087 | 10.3715 |
| 85.58421 | 72.90673 | 12.56855 |

TABLE 3

140 ml. Lactated Ringer's solution; 10.0 ml.
Na+ CMC aged slurry (75.6 mg Solid)

| Cu, mg./l. | Cu mg/l. | Solids-Cu mg/g |
|---|---|---|
| 0 | | |
| 0.214533 | 0.084903 | 0.02572 |
| 0.429067 | 0.154381 | 0.054501 |
| 0.858133 | 0.278515 | 0.115004 |
| 1.2872 | 0.457197 | 0.164683 |
| 2.145333 | 0.799266 | 0.267077 |
| 4.290667 | 1.64828 | 0.524283 |
| 6.436 | 2.601365 | 0.76084 |
| 10.72667 | 4.372258 | 1.260796 |
| 17.16267 | 7.009866 | 2.014445 |
| 25.744 | 10.38834 | 3.046758 |
| 34.32533 | 14.11884 | 4.009224 |
| 42.90667 | 18.44879 | 4.852754 |
| 64.36 | 28.88827 | 7.038042 |
| 85.81333 | 38.64922 | 9.357958 |
| 128.72 | 59.10773 | 13.81196 |

TABLE 4

Add 50.0 ml. Na+ CMC solution to 100 ml. Lactated Ringers solution (378.3 mg. Solid)

| Cu, mg./l. | Copper mg./l. | Solids-Cu mg/g |
|---|---|---|
| 0 | | |
| 0.214533 | 0.202998 | 0.004577 |
| 0.429067 | 0.26174 | 0.0664 |
| 0.858133 | 0.402883 | 0.180655 |
| 1.2872 | 0.523483 | 0.303062 |
| 2.145333 | 0.71786 | 0.566458 |
| 4.295386 | 1.586918 | 1.074789 |
| 6.445439 | 2.405326 | 1.603219 |
| 10.75799 | 4.187934 | 2.607165 |
| 17.18326 | 7.180194 | 3.969471 |
| 25.65561 | 11.05211 | 5.79504 |
| 34.12796 | 15.39118 | 7.43523 |
| 42.60031 | 19.54163 | 9.15027 |
| 64.09226 | 30.78253 | 13.21815 |
| 85.58421 | 43.53319 | 16.68691 |
| 128.7054 | 76.38203 | 20.76324 |

TABLE 5

146 ML. LACTATED Ringer's solution; 4.00 ml. Na+ CMC aged slurry (30.3 mg. Solid)

| Cu, mg./l. | CU, mg./l. | Solids-Cu mg/g |
|---|---|---|
| 0 | | |
| 0.214533 | 0.103357 | 0.05522 |
| 0.429067 | 0.214831 | 0.106409 |
| 0.858133 | 0.403121 | 0.225999 |
| 1.2872 | 0.621378 | 0.330706 |
| 2.145333 | 1.069327 | 0.53444 |
| 4.295386 | 2.20521 | 1.038167 |
| 6.445439 | 3.319862 | 1.552439 |
| 10.75799 | 5.713137 | 2.505722 |
| 17.18326 | 9.527134 | 3.802712 |
| 25.65561 | 14.45603 | 5.562705 |
| 34.12796 | 19.64725 | 7.192406 |
| 42.60031 | 23.91773 | 9.279427 |
| 64.09226 | 36.86721 | 13.52238 |
| 85.58421 | 53.36134 | 16.00474 |
| 128.7054 | 81.60755 | 23.39297 |

TABLE 6

| Total Cu Added micro-moles/L | Dissolved Cu micro-moles/L | Solids Cu micro-moles/g | Dissolved/solids | | mg. Ca++ CMC |
|---|---|---|---|---|---|
| 9.84 | 5.47 | 0.001276037 | 4286.710908 | 300 | ml |
| 16.41 | 9.44 | 0.002035235 | 4638.285988 | | |
| 32.95 | 19.87 | 0.00381935 | 5202.456167 | | |
| 49.5 | 29.6 | 0.005810785 | 5093.976549 | | |
| 82.5 | 51.5 | 0.009051976 | 5689.365591 | | |
| 131.7 | 81.2 | 0.014745961 | 5506.592739 | | |
| 196.8 | 120.8 | 0.022191941 | 5443.417544 | | |
| 261.7 | 161.7 | 0.029199922 | 5537.686 | | |
| 326.6 | 201.8 | 0.036441503 | 5537.642094 | | |
| 492.4 | 311.5 | 0.052822659 | 5897.090474 | | |
| 657.6 | 427.3 | 0.067247421 | 6354.147055 | | |
| 982 | 644 | 0.098695737 | 6525.104536 | | |

TABLE 7

| Total Cu Added micro-moles/L | Dissolved Cu micro-moles/L | Solids Cu micro-moles/g | Dissolved/solids | 1033.5 | mg. Ca++ CMC |
|---|---|---|---|---|---|
| 6.56 | 2.17 | 0.000637155 | 3405.763098 | 150 | ml |
| 13.12 | 4.36 | 0.001271408 | 3429.269406 | | |
| 19.69 | 6.16 | 0.001963716 | 3136.910569 | | |
| 32.82 | 10.07 | 0.003301887 | 3049.771429 | | |
| 65.88 | 20.22 | 0.006626996 | 3051.156373 | | |
| 98.93 | 30.05 | 0.009997097 | 3005.872532 | | |
| 164.8 | 48.8 | 0.016835994 | 2898.551724 | | |
| 263 | 79.1 | 0.026690856 | 2963.561718 | | |
| 392.7 | 117.6 | 0.039927431 | 2945.343511 | | |
| 522.1 | 155.4 | 0.053222061 | 2919.841833 | | |
| 651.1 | 192.3 | 0.06658926 | 2887.853095 | | |

TABLE 8

| Total Cu Added micro-moles/L | Dissolved Cu micro-moles/L | Solids Cu micro-moles/g | Dissolved Solids | 218.9 | mg. Ca++ CMC |
|---|---|---|---|---|---|
| 13.13 | 6.63 | 0.004483783 | 1478.662252 | 151 | ml |
| 19.69 | 9.53 | 0.007008497 | 1359.777989 | | |
| 26.25 | 11.51 | 0.010167839 | 1132.000593 | | |
| 32.82 | 14.55 | 0.012602878 | 1154.4982 | | |
| 65.88 | 30.04 | 0.024722887 | 1215.068443 | | |
| 98.93 | 44.83 | 0.037318867 | 1201.26905 | | |
| 164.8 | 76.07 | 0.061207081 | 1242.83006 | | |
| 263 | 122.4 | 0.096987666 | 1262.016147 | | |

TABLE 9

| Total Cu Added micro-moles/L | Dissolved Cu micro moles/L | Solids Cu micro-moles/g | Dissolved Solids | 56 | mg. Ca++ CMC |
|---|---|---|---|---|---|
| 13.13 | 10.47 | 0.007125 | 1469.473684 | 150 | ml. |
| 19.69 | 16.13 | 0.009535714 | 1691.535581 | | |
| 32.82 | 27.8 | 0.013446429 | 2067.463479 | | |
| 65.88 | 57.58 | 0.022232143 | 2589.943775 | | |
| 98.93 | 89.41 | 0.0255 | 3506.27451 | | |
| 164.8 | 152.8 | 0.032142857 | 4753.777778 | | |
| 263 | 238.2 | 0.066428571 | 3585.806452 | | |
| 392.7 | 362 | 0.082232143 | 4402.171553 | | |
| 522.1 | 484.8 | 0.099910714 | 4852.33244 | | |

Ag+ Na+CMC Equilibrium Studies:

Basically the same procedure used to study the equilibrium behavior Cu++ with Na+ CMC described above was used to evaluate the equilibrium behavior of Silver (Ag+) in the presence of Na+ CMC.

Figure 3:
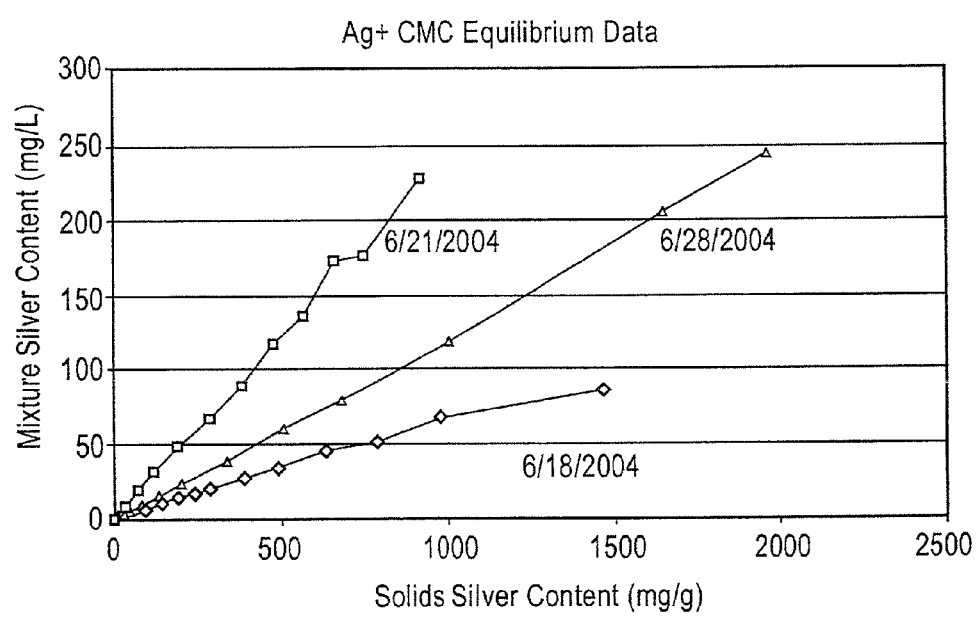
FIG. 3 is a graph showing the effect of Na+ CMC solids Ag+ content on dissolved Ag+ content.

The results of these tests are included as Tables 10-12, which are plotted in FIG. 3.

TABLE 10

| Silver/ Sulfide ISE | | 103.4 mg Na+ CMC | 100 ml | |
|---|---|---|---|---|
| Ag+ Added mg/Lit | mV Mixture | log Ag+ mixture | Ag+ mg/Lit mixture | Ag solids mg/g. |
| 5.39 | 347.3 | 0.51311475 | 3.25922809 | 49.16579798 |
| 10.78 | 368.1 | 0.85409836 | 7.14658166 | 97.72176538 |
| 16.16 | 379.3 | 1.03770492 | 10.9069901 | 146.3038931 |
| 21.53 | 386.6 | 1.15737705 | 14.3673625 | 195.0802306 |
| 26.9 | 391.6 | 1.23934426 | 17.3517892 | 244.3186513 |
| 32.26 | 395.6 | 1.30491803 | 20.1798546 | 293.6117916 |

TABLE 10-continued

| Silver/Sulfide ISE | 103.4 mg Na+ CMC | | 100 ml | |
|---|---|---|---|---|
| Ag+ Added mg/Lit | mV Mixture | log Ag+ mixture | Ag+ mg/Lit mixture | Ag solids mg/g. |
| 42.98 | 403.1 | 1.42786885 | 26.783594 | 391.2780641 |
| 53.67 | 409.1 | 1.52622951 | 33.5915086 | 488.454846 |
| 69.66 | 416.5 | 1.64754098 | 44.4161574 | 633.1881967 |
| 85.61 | 419.7 | 1.7 | 50.1187234 | 782.5060938 |
| 106.8 | 427 | 1.81967213 | 66.0194848 | 972.7966167 |
| 159.41 | 433.8 | 1.93114754 | 85.3389983 | 1464.816506 |

TABLE 11

| Silver/Sulfide ISE Ag+ | 1005.2 mg Na+ CMC | | 100 ml | |
|---|---|---|---|---|
| Added mg/Lit | mV Mixture | log Ag+ mixture | Ag+ mg/Lit mixture | Ag solids mg/g. |
| 5.39 | 106.2 | −3.4393443 | 0.00036363 | 5.133298702 |
| 10.78 | 306.4 | −0.157377 | 0.69602197 | 10.20037886 |
| 21.53 | 355.8 | 0.65245902 | 4.49219931 | 20.0769334 |
| 42.98 | 372.4 | 0.92459016 | 8.40601506 | 40.13276047 |
| 85.61 | 393.5 | 1.2704918 | 18.6419699 | 79.75790763 |
| 127.9 | 407.5 | 1.5 | 31.6227766 | 118.7978308 |
| 211.51 | 418 | 1.67213115 | 47.0036028 | 196.9615616 |
| 314.18 | 427.3 | 1.82459016 | 66.7713511 | 292.8598713 |
| 414.88 | 435 | 1.95081967 | 89.2934642 | 386.6196701 |
| 513.67 | 442.1 | 2.06721311 | 116.738233 | 478.0915969 |
| 610.58 | 446.1 | 2.13278689 | 135.764707 | 568.5747899 |
| 705.69 | 452.6 | 2.23934426 | 173.517892 | 655.5602008 |
| 799.04 | 453.1 | 2.24754098 | 176.823908 | 744.150104 |
| 980.64 | 459.8 | 2.35737705 | 227.70735 | 912.2564429 |

TABLE 12

| Silver/Sulfide ISE Ag+ | 192.7 mg Na+ CMC | | 150 ml | |
|---|---|---|---|---|
| Added mg/Lit | mV Mixture | log Ag+ mixture | Ag+ mg/Lit mixture | Ag solids mg/g. |
| 0.719 | 291.8 | −0.3967213 | 0.40112404 | 3.418948595 |
| 1.44 | 310.1 | −0.0967213 | 0.80034768 | 6.849755311 |
| 2.16 | 320.5 | 0.07377049 | 1.18514228 | 10.28660435 |
| 3.59 | 331.8 | 0.25901639 | 1.81558419 | 17.21672221 |
| 7.19 | 351.4 | 0.58032787 | 3.80476527 | 34.35020866 |
| 10.78 | 362.5 | 0.76229508 | 5.78488969 | 51.43885079 |
| 17.95 | 376.4 | 0.99016393 | 9.77606171 | 85.54016992 |
| 28.69 | 388.8 | 1.19344262 | 15.6114277 | 136.7321528 |
| 42.98 | 399.4 | 1.36721311 | 23.2923397 | 204.9099587 |
| 71.44 | 412.7 | 1.5852459 | 38.4809603 | 340.7776645 |
| 106.8 | 424.1 | 1.77213115 | 59.17403 | 508.1675947 |
| 141.93 | 431.6 | 1.89508197 | 78.5383851 | 675.3982472 |
| 211.51 | 442.4 | 2.07213115 | 118.067712 | 1005.707541 |
| 347.97 | 457.1 | 2.31311475 | 205.64339 | 1645.684959 |
| 414.88 | 461.7 | 2.38852459 | 244.638379 | 1962.554453 |

Conclusions:

Data from the equilibrium studies indicates that both Na+ CMC and Ca++ CMC will function as ion exchange resins for Cu+. It was also demonstrated that Na+ CMC will function as an ion exchange resin for Ag+.

Variability in the dissociation constants (shown as the line slopes of FIGS. 1-3) will need to be investigated in subsequent testing, and it is possible that the particle size of the CMC salts is a factor.

Example 4

Testing of Hydrocolloid Wound Dressings Containing Copper Salts of CMC

The copper and silver salts of CMC obtained in Examples 1 and 2 may be incorporated into a hydrocolloid wound dressing. A hydrocolloid wound dressing prepared with CMC that has not been substituted with copper or silver will be prepared as a control.

The efficacy of wound dressings containing copper salts of CMC in preventing infection will be compared with the anti-infective efficacy of wound dressings containing silver salts, and standard wound dressings not containing anti-infective agent.

The prepared hydrocolloid wound dressings will be evaluated for their ability to release copper and silver ions into a simulated wound fluid, in order to confirm the efficacy of the adhesive matrix in delivering the ions, and determine target ion concentrations for commercial products.

Zone of inhibition testing will be carried out to determine the effectiveness of varying concentrations of copper ions on growth of several microbial strains.

Animal testing will be conducted, including dermal irritation, dermal sensitization, acute oral toxicity, acute intracutaneous reactivity, and fibroblastic cytotoxicity of the CMC-copper salt and hydrocolloids formulated therewith. It is expected that these tests will show that the CMC-copper salts and hydrocolloids formulated therewith are well-tolerated.

A swine-based dermal wound healing study will be conducted to compare the efficacy of the hydrocolloid wound dressings. The tests may show a strong anti-infective activity of the wound dressing containing copper salts of CMC, which is expected to be similar to or slightly more effective than the anti-infective wound dressings containing silver salts, and superior to the anti-infective efficacy of control wound dressings.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

The invention claimed is:

1. A wound treatment article comprising a system,
   wherein the system includes an anti-infective agent which comprises a salt comprising a water-soluble ion exchange materials and copper ions;
   wherein the copper ions are releasable from the system;
   wherein a total amount of copper provided by the system is from 0.0001% to 0.0005% by weight of the system, such that the system can release an amount of copper necessary to exchange with cations present in a surrounding fluid;

wherein the system is free of silver; and wherein the would treatment article is provided in a form selected from the group consisting of wound dressings, gauzes, and bandages.

2. The would treatment article of claim 1, wherein the water-soluble ion exchange materials are cellulose derivatives selected from the group consisting of carboxymethyl cellulose (CMC), ethylcellulose (EC), methylcellulose (MC), hydroxypropyl cellulose (HPC), hydroxypropyl methyl cellulose (HPMC), hydroxyethyl methyl cellulose (NEMC), cellulose acetate, and cellulose triacetate.

3. The would treatment article of claim 1, wherein the salt comprises copper (I) and/or copper (II) ions.

4. The wound treatment article of claim 1, wherein the total amount of the copper provided by the system is such that upon contacting the wound treatment article with a source of liquid and ions, copper ions associated with the ion exchange materials are exchanged with ions in the source of liquid and ions.

5. The wound treatment article of claim 4, wherein the total amount of the copper provided by the system is such that an equilibrium of copper ions is established in the source of liquid.

6. The wound treatment article of claim 5, wherein the total amount of the copper provided by the system is such that the equilibrium of copper ions is established at a level effective for killing microbes.

* * * * *